United States Patent
Cheng et al.

(10) Patent No.: US 8,172,996 B2
(45) Date of Patent: May 8, 2012

(54) ENZYME ELECTRODE AND METHOD FOR PRODUCING THE SAME

(75) Inventors: Chean-Yeh Cheng, Tao-Yuan (TW); Kuo-Chung Chang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 505 days.

(21) Appl. No.: 12/421,565

(22) Filed: Apr. 9, 2009

(65) Prior Publication Data
US 2010/0219072 A1    Sep. 2, 2010

(30) Foreign Application Priority Data
Feb. 27, 2009  (TW) ............................... 98106428 A (51) Int. Cl.
*G01N 27/327*    (2006.01)
(52) U.S. Cl. .............. 204/403.11; 204/403.14; 427/2.13
(58) Field of Classification Search ............. 204/403.01, 204/403.11, 403.14; 427/2.13
See application file for complete search history.

(56) References Cited

U.S. PATENT DOCUMENTS
5,286,364 A * 2/1994 Yacynych et al. ............... 205/83
5,804,047 A * 9/1998 Karube et al. ........... 204/403.04

OTHER PUBLICATIONS
Gooding et al, Trends in Analytical Chemistry 18(8), 1999, pp. 525-533.*
Kim et al, Journal of the Korean Electrochemical Society 2(1), 1999, pp. 27-30.*
Godjevargova et al, Journal of Molecular Catalysis B: Enzymatic 38, 2006, pp. 59-64.*

* cited by examiner

*Primary Examiner* — Kaj K Olsen
(74) *Attorney, Agent, or Firm* — Stout, Uxa, Buyan & Mullins, LLP (57) ABSTRACT

An enzyme electrode and its producing method are disclosed. The method includes providing a substrate having a carbon surface; forming a gold surface on the carbon surface and forming an electrode; modifying the gold surface by L-cysteine; modifying the gold surface by N,N'-dicyclohexylcarbodiimide; and chemically bonding the modified gold surface with a glucose oxidase.

14 Claims, 6 Drawing Sheets

ENZYME ELECTRODE AND METHOD FOR PRODUCING THE SAME

CROSS-REFERENCE

The entire contents of Taiwan Patent Application No. 098106428, filed on Feb. 27, 2009, from which this application claims priority, is incorporated herein by reference.

FIELD OF THE INVENTION

The present invention relates to an enzyme electrode and a method for producing the enzyme electrode.

DESCRIPTION OF THE PRIOR ART

Glucose analysis has been important in the food and drink industry and in medical diagnoses, such as the determination of blood sugar for diabetes, for many years. In the past, scientists have analyzed the total sugars with optical rotation methods or colorimetry methods. In recent years, instrumental methods, such as high-performance liquid chromatography (HPLC) or mass spectrometry (MS), have been used extensively for separating and analyzing glucose. However, the enzyme electrode method can offer advantages of substrate specificity, easy operation, low cost, simple and portable instrumentation, and faster analysis can make the glucose enzyme electrode method a best choice for glucose determination.

The initial concept of the glucose enzyme electrode can be traced back to the works of Clark and Lyons in 1962 (Wang, J., 2008. Chemical Review 108, pp. 814-825). They disclose that glucose is oxidized to gluconolactone by oxygen via the catalysis of glucose oxidase accompanied with the production of the hydrogen peroxide. Then the hydrogen peroxide is oxidized automatically to release the electron, and this current is proportional to the amount of glucose; however, the current generation depends on oxygen that can be disturbed by the fluctuation of the oxygen in the air. In 1974, Schlapfer improved the glucose biosensor by replacing the oxygen with an artificial mediator for eliminating the dependence of oxygen in the air for glucose oxidation (Wang, J., 2008. Chemical Review 108, pp. 814-825). Schlapfer's methodology is shown in the following equations (1), (2) and (3), and has been adopted by most researchers who design the modern enzyme electrode biosensor.

glucose+glucose oxidase$_{(ox)}$→gluconolactone+glucose oxidase$_{(red)}$  Eq. (1)

glucose oxidase$_{(red)}$+2 mediator$_{(ox)}$→glucose oxidase$_{(ox)}$+2 mediator$_{(red)}$  Eq. (2)

2 mediator$_{(red)}$→2 mediator$_{(ox)}$+2 $e^-$  Eq. (3)

In addition, to set up a stable long-term reusable enzyme electrode, the immobilization between an enzyme and the electrode will be a very important factor. Today many methods are used for enzyme immobilization, such as the physical adsorption method, the cross-linking method, the encapsulation method, and the chemical bonding method. The material of the enzyme electrode also plays an important role in the enzyme immobilization. For glucose analysis, metal (especially gold) and non-metal carbon are two major materials currently employed for producing the enzyme electrodes. However, the gold electrode is expensive, and the carbon electrode lacks stability and shows poor reliability.

Although many methods have been disclosed, so far no enzyme electrode and its producing method would appear to meet the requirements of a test accuracy comparable with the instrument analyses, a wide detectable concentrate range, and an excellent enzyme immobilization such that the electrode has good stability and long-term reusable capability.

Therefore, it would be advantageous to provide an enzyme electrode and its producing method for improving the deficiencies of prior-art approaches and meeting the above-mentioned requirements.

SUMMARY OF THE INVENTION

The object of the present invention is to provide an enzyme electrode and its producing method. The enzyme electrode can be employed for detecting glucose. The enzyme electrode can meet one or more (e.g., all) of the requirements that the analysis accuracy is comparable with the instrument analyses, the detectable concentrate range is wide, and the enzyme immobilization is excellent such that the enzyme electrode has good stability and long-term reusable capability.

According to the object, the present invention provides a method for producing an enzyme electrode. The method comprises: providing a substrate having a carbon surface; forming a gold surface on the carbon surface and thus forming an electrode; modifying the gold surface by L-cysteine to bond covalently between the gold particles of the gold surface and the sulphydryl group of L-cysteine, thereby forming a first electrode having a first modified surface; modifying the first modified surface by N,N'-dicyclohexylcarbodiimide, the L-cysteine of the first modified surface and the N,N'-dicyclohexylcarbodiimide being dehydrated to form covalent bonds, thereby forming a second electrode having a second modified surface; and contacting the second modified surface with the glucose oxidase, an amide bond being formed between the L-cysteine group of the second modified surface and the glucose oxidase, thereby forming a third electrode having a third modified surface.

According to the object, the present invention provides an enzyme electrode produced by the above method, and the enzyme electrode is applied to an electrochemical sensor for glucose analysis; the electrochemical sensor comprises a working electrode and a reference electrode, and the enzyme electrode functions as the working electrode.

According to the object, the present invention provides an enzyme electrode, which comprises a substrate structure and a modified structure. The substrate structure comprises a pencil lead, a carbon layer covering the pencil lead, and a gold layer covering the carbon layer. Additionally, the above-mentioned modified structure is chemically bounded with the gold layer, and the modified structure comprises an L-cysteine group and a glucose oxidase group, with an Au—S covalent bond being formed between the gold layer and the L-cysteine group and an amide bond being covalently bonded between the L-cysteine group and the glucose oxidase group.

BRIEF DESCRIPTION OF THE DRAWINGS

FIGS. 5A-5C demonstrate the long-term stability and reusability of the enzyme electrode according to the present invention, wherein

DESCRIPTION OF THE PREFERRED EMBODIMENT

A detailed description of the present invention will be provided in the context of the following embodiments, which are not intended to limit the scope of the present invention and which can be adapted for other applications. To the extent drawings are illustrated in detail, it is appreciated that the quantity of the disclosed components may be greater or less than that disclosed, except for instances expressly restricting the amount of the components.

Figure 1:
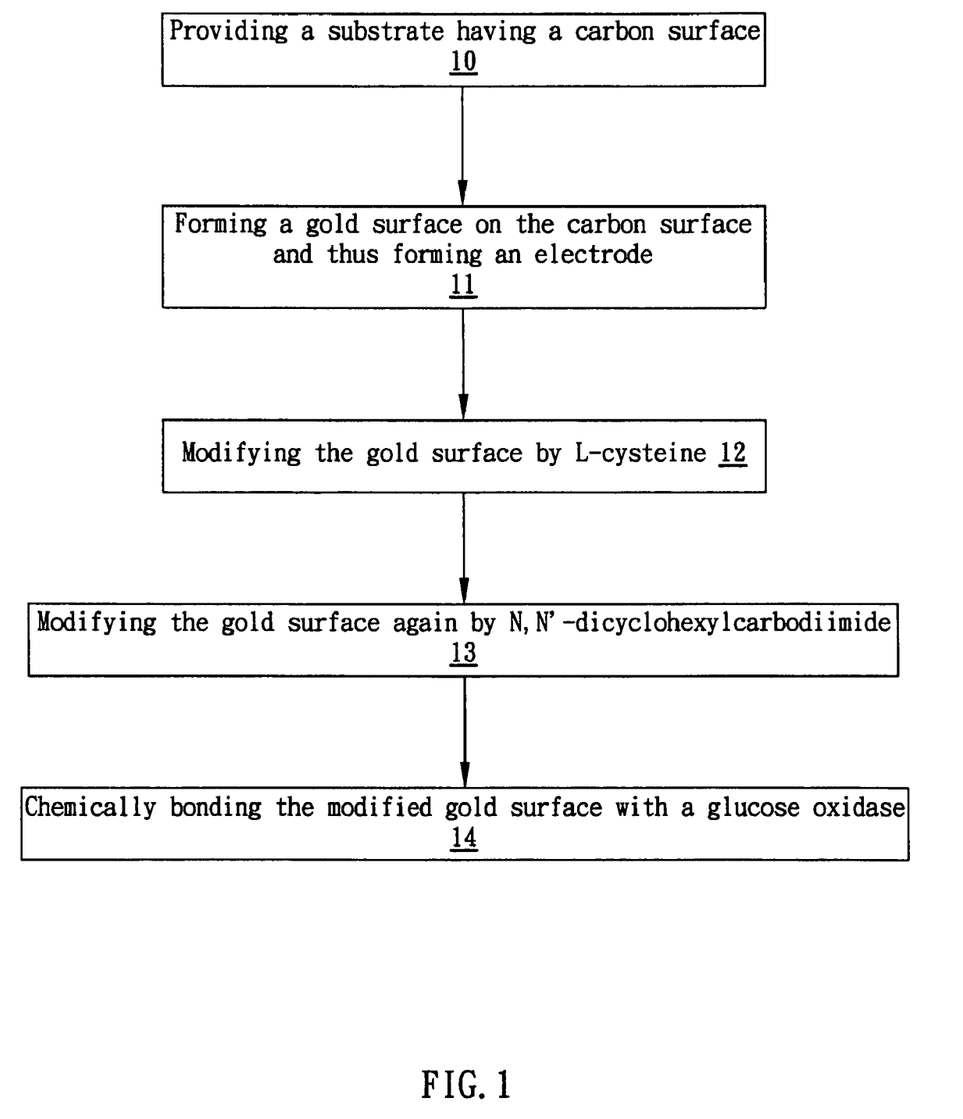
FIGS. 1-2 show an enzyme electrode and its producing method according to one embodiment of the present invention.
Figure 2:
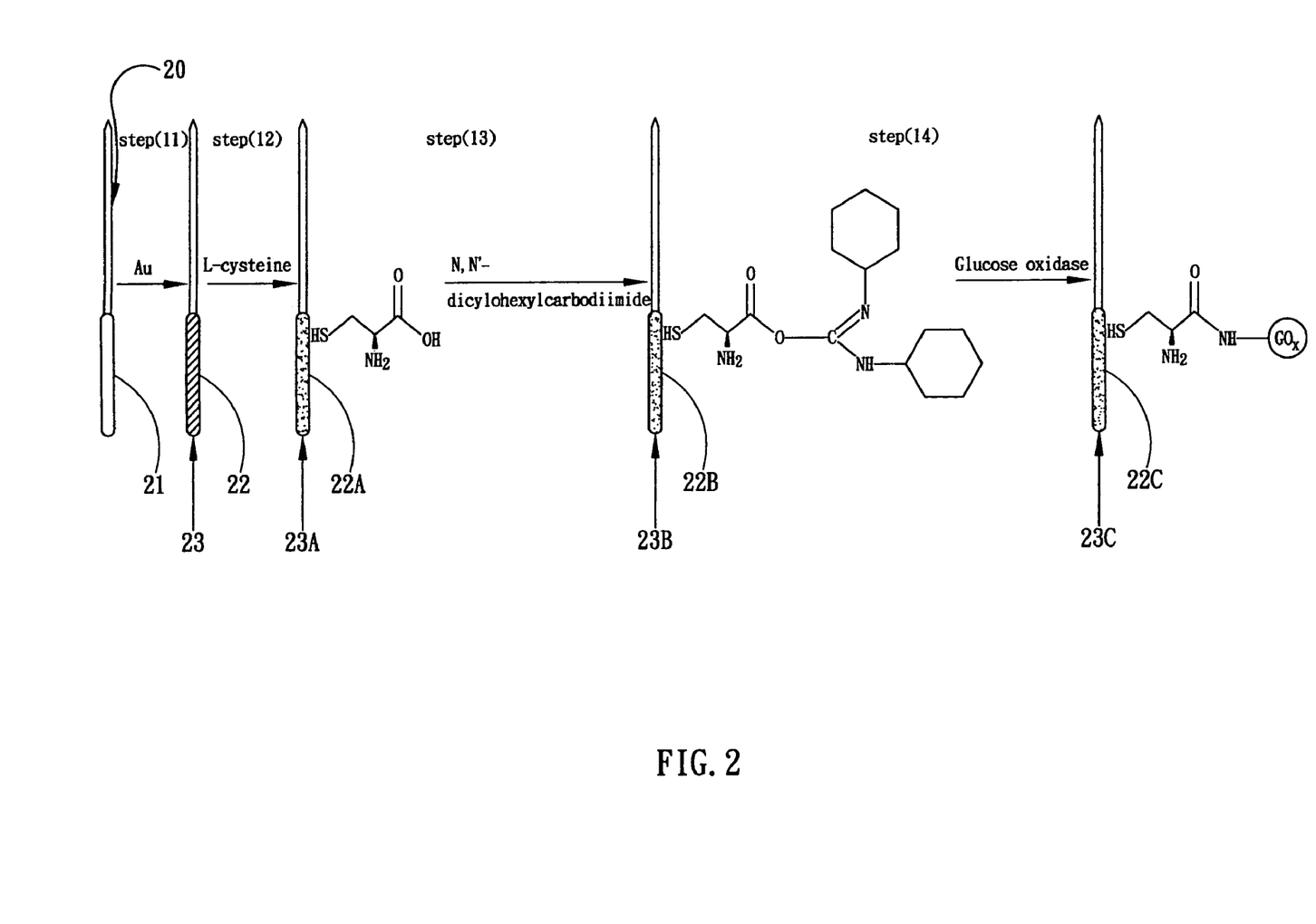

FIG. 1 and FIG. 2 show an enzyme electrode and its producing method according to one embodiment of the present invention. At step 10, a substrate 20 having a carbon surface 21 is provided, where at least a portion of the surface or even the whole surface of substrate 20 has the carbon surface 21, and the degree of carbon purity is better as higher as possible. Although the substrate 20 is rod-shaped as shown in FIG. 2, it can comprise any other shape such as a slice-shape. In addition, the substrate 20 can be made of any material, such as any metal or non-metal materials. In one embodiment, the substrate 20 is made of pencil lead, and then a high purity of carbon paste is coated on the pencil lead followed by drying at about 120° C. to form the carbon surface 21. At step 11, an electrode 23 is formed by forming a gold surface 22 on the carbon surface 21 of the substrate 20. Many methods can be employed for forming the gold surface 22, and it should not be limited. For example, the gold surface 22 can be formed by deposition, ink-inject, electrodeposition, or screen-printing methods. In the preferred embodiment, the gold surface 22 is formed by electrodeposition in which the gold ions were reduced from the hydrogen tetrachloroaurate trihydrate solution ($HAuCl_4 \cdot 3H_2O$) and deposited on the carbon surface 21. In another embodiment, the electrode 23 may be further rinsed after the electrodeposition is finished. For example, deionized distilled water may be used to remove the unreduced hydrogen tetrachloroaurate trihydrate compounds. At step 12, the gold surface 22 is modified by L-cysteine. For example, the gold surface 22 can be immersed in 20 mM L-cysteine solution for one hour at 25° C. to bond covalently the gold particles and the sulphydryl group of L-cysteine, thus forming a first modified surface 22A and forming a first electrode 23A. After being modified by L-cysteine, the first electrode 23A may be thoroughly rinsed with deionized distilled water to remove physically adsorbed L-cysteine. At step 13, the first modified surface 22A is further modified by N,N'-dicyclohexylcarbodiimide. The L-cysteine of the gold surface and the N,N'-dicyclohexylcarbodiimide are dehydrated to form covalent bonds, thus forming a second modified surface 22B and forming a second electrode 23B. For example, the first electrode 23A having the first modified surface 22A is immersed in the 40 mM N,N'-dicyclohexylcarbodiimide dissolved in chloroform for one hour at 40° C. At step 14, the second modified surface 22B is chemically bonded with glucose oxidase. The second modified surface 22B is contacted with the glucose oxidase, an amide bond being formed between the L-cysteine group of the second modified surface 22B and the glucose oxidase; thus enzymes are chemically bonded on the electrode surface, forming a third electrode 23C having a third modified surface 22C. For example, in one embodiment the second modified surface 22B is immersed in the 40 mM glucose oxidase solution that was prepared with phosphate buffer solution (PBS) at 25° C. for 24 hours, so that amide bonds or peptide bonds are formed between the L-cysteine group of the second modified surface 22B and the glucose oxidase. The glucose oxidase may be obtained from the culture of *Aspergillus niger*, EC 1.1.3.4, GOx type VII, 180200 units/g solid.

Experiments are conducted in an electrochemical cell consisting of a three-electrode system for qualifying the enzyme electrode produced by the method of the present invention. The three-electrode electrochemical cell may comprise a platinum wire as the counter electrode, a silver/silver chloride electrode (Ag/AgCl) as the reference electrode, and the enzyme electrode of the present invention as the working electrode. The quantification of glucose is based on the standard addition calibration method, which can be used to find the sensitivity, limit of detection, and linear concentration range. The three-electrode electrochemical cell employs 8 mL 0.1 M pH 7.0 PBS as the background solution, which contains 0.1 mM hydroxymethylferrocene ($FeC_{11}H_{12}O$, also referred to as ferrocene methanol) as the mediator. The hydroxymethylferrocene may be obtained from business or known product, such as the Hydroxymethylferrocene (Fc) (99.0%), Strem Chemicals, Newburyport, USA. A spiked sample analysis is also carried out for checking the interference effect and the accuracy. The glucose concentrations measured by the enzyme electrode are also compared with the HPLC to compare the precision and accuracy.

Further, many factors affecting the measuring accuracy are also checked by the experiments. The experimental results show that when the pH of phosphate buffer concentration is 6.0, the current signal will be a bit weak; and when the pH of phosphate buffer concentration is 6.5, 7.0, 7.5, or 8.0, the current signal will be strong. All experimental results are obtained at 95% confidence level. The experimental results show that by maintaining a constant buffer pH at 7.0, a constant mediator Fc concentration at 0.2 mM, and a constant concentration of the PBS at 0.1 M, an excellent sensitivity can be obtained. The experimental results indicate that when the concentration of the mediator is equal or greater than 0.1 mM, the performance of the enzyme electrode is satisfactory, but the limit of detection is lowered when the concentration of the mediator is smaller than 0.1 mM. The experimental results indicate that the glucose oxidase concentration at 30 μM has the best linear correlation coefficient $r^2$ (0.9999) over the standard glucose oxidase concentration range from 0 to 33.41 mM, a higher sensitivity (10.00 μA $mM^{-1}$), and an intermediate LOD (22.3 μM).

Figure 3:
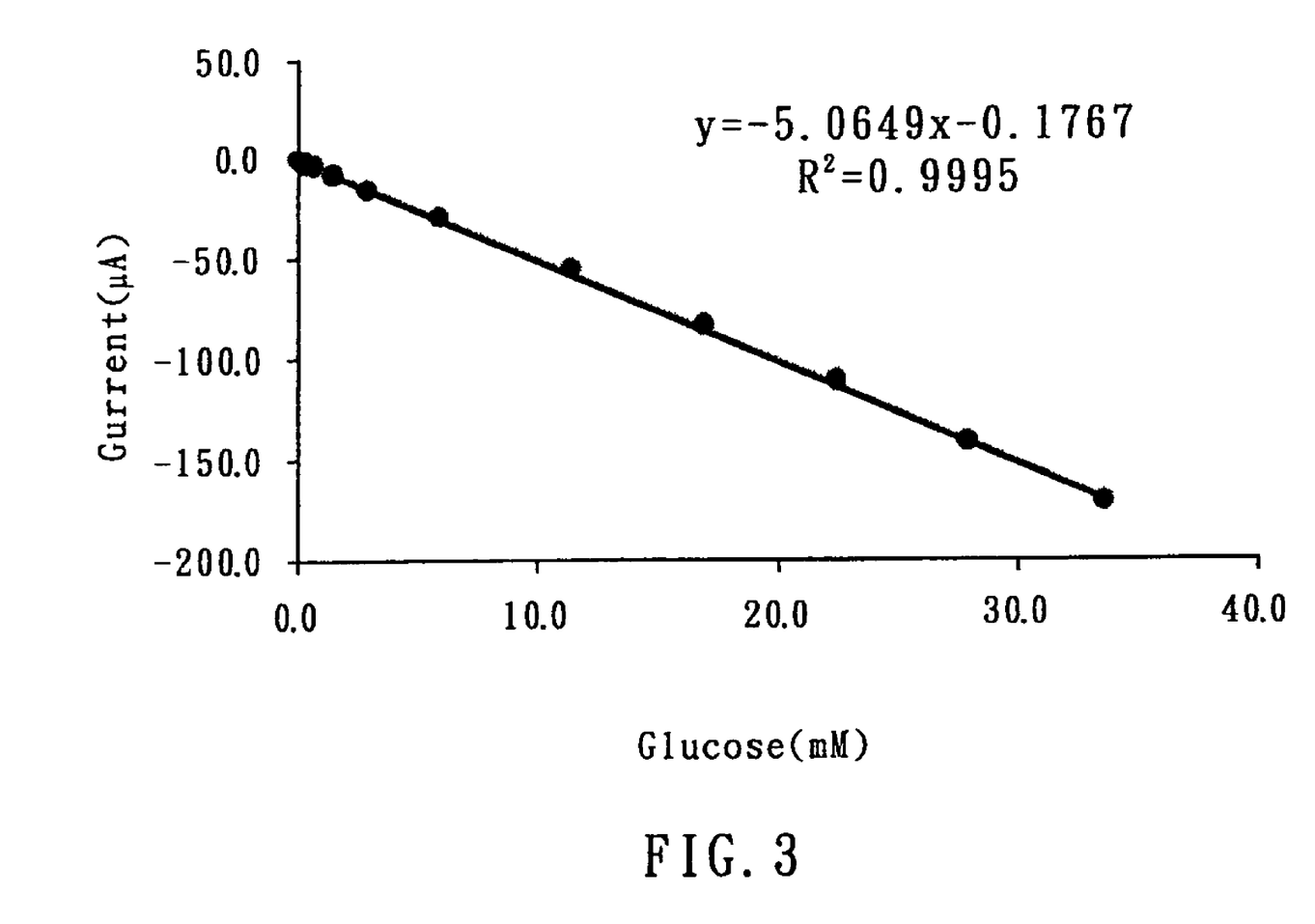
FIG. 3 is a glucose standard addition calibration curve obtained by calculating the corresponding glucose concentration at each standard addition current.

FIG. 3 is a glucose standard addition calibration curve obtained by calculating the corresponding glucose concentration at each standard addition current. The glucose standard addition calibration curve possesses a wide linear glucose concentration range (0 to 33.41 mM) that exhibits an excellent linearity ($r^2$=0.9995). The standard addition calibration curve also shows a high detection sensitivity (5.06 μA $mM^{-1}$) and a low LOD (14.2 μM).

Figure 4:
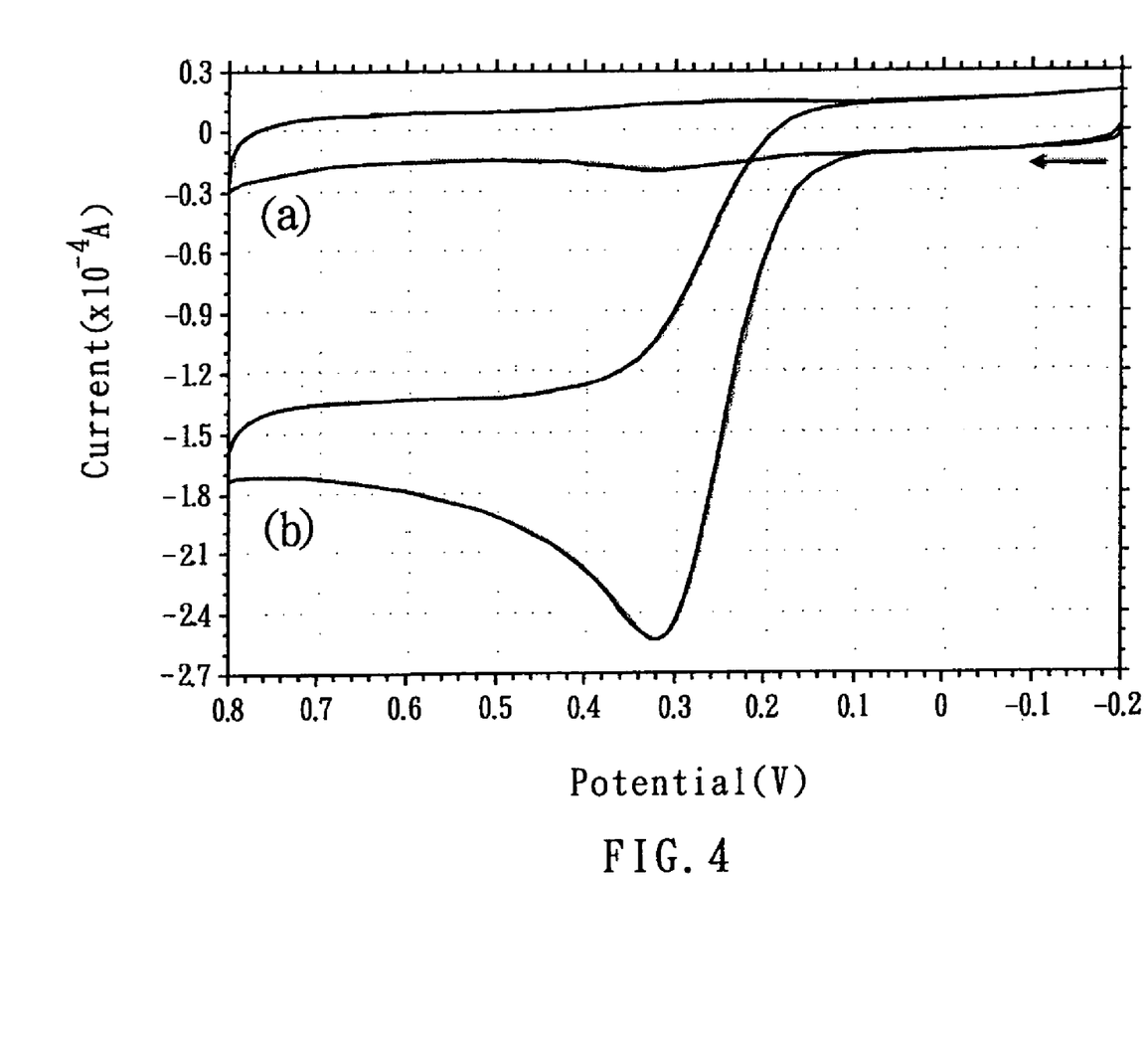
FIG. 4 is a cyclic voltammetry (CV) diagram of the enzyme electrode according to the present invention.

FIG. 4 is a cyclic voltammetry (CV) diagram of the enzyme electrode according to the present invention, the CV analysis being measured at 35° C. Curve (a) shows cyclic voltammogram of the glucose sensor electrode with a background solution containing 0 mM glucose, and curve (b) shows cyclic voltammogram of the glucose sensor electrode with a background solution containing 33.41 mM glucose. The background solution used in (a) and (b) is 0.1 M PBS (pH7.0) containing 0.1 mM hydroxymethylferrocene (Fc). From the cyclic voltammogram (b), the oxidation-reduction potential of the Fc is at 0.33 V. The strong anodic current in cyclic voltammogram (b) obtained with 33.41 mM glucose standard solution added into the 0.1 M pH 7.0 PBS and 0.1 mM Fc is compared with the background solution shown in cyclic voltammogram (a) to prove a successful immobilization of the glucose oxidase on the modified surface of the enzyme electrode.

Figure 5A:
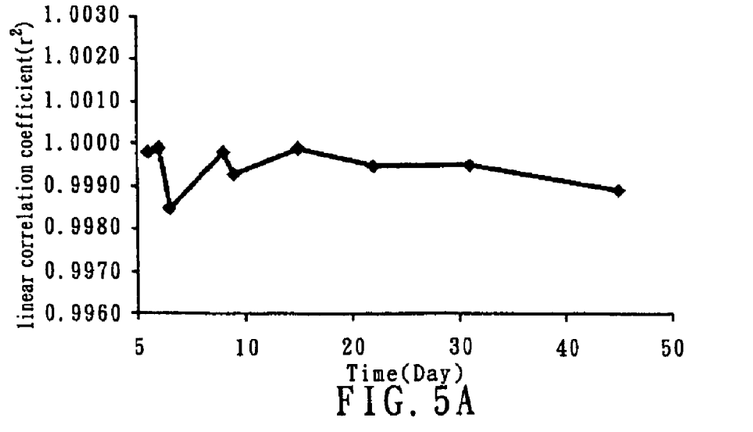
FIG. 5A shows a variation of the linearity of the calibration curve ($r^2$)
Figure 5B:
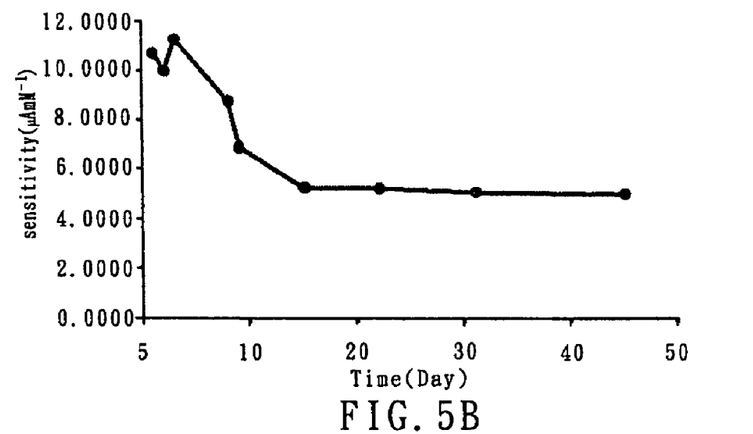
FIG. 5B shows a variation of the detection sensitivity.
Figure 5C:
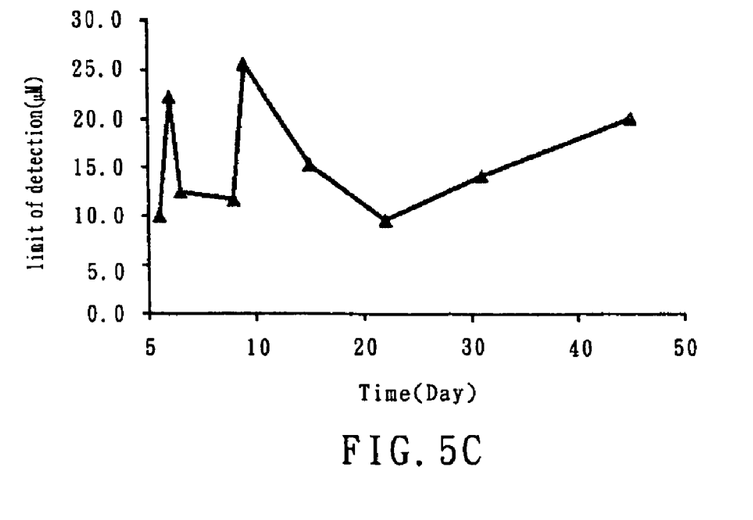
FIG. 5C shows a variation of limit of detection (LOD).

FIG. 5A to FIG. 5C demonstrate the long-term stability and reusability of the enzyme electrode according to the present invention, wherein FIG. 5A shows a variation of the linearity of the calibration curve ($r^2$), FIG. 5B shows a variation of the detection sensitivity, FIG. 5C shows a variation of limit of detection (LOD), and all of the three performance parameters are checked over a long period of 45 days. After each use, the enzyme electrode is stored in 0.1 M pH 7.0 PBS at room temperature. FIG. 5A shows that within the testing period, the calibration curve maintains an excellent linearity ($r^2 \geqq 0.9985$) with most of the $r^2$ values being larger than 0.9990. In FIG. 5B, the detection sensitivity was larger than 10 $\mu$A mM$^{-1}$ during the first three testing days; at 15 days the detection sensitivity dropped to about 50% of the first day's sensitivity and stabilized at a value a little larger than 5 $\mu$A mM$^{-1}$. FIG. 5C shows that during the 45-day testing period, the LOD varied significantly from about 10 $\mu$M to 26 $\mu$M. In addition, the performance of the enzyme electrode was further examined to 94 days. The experimental results show a decrease in glucose oxidase activity narrowing down the linear glucose concentration range to about 0 mM to 16.67 mM, which has the corresponding sensitivity 4.98 $\mu$A mM$^{-1}$ and has LOD 20.1 $\mu$M. Moreover, the performance of the enzyme electrode was further extended to 228 days. The experimental results show that because the decreased activity of the glucose oxidase, the linear concentration range is narrowed down to about 0 mM to 16.67 mM, with $r^2=0.9888$. According to the experimental results elucidated above, the enzyme electrode of the present invention has a far greater long-term stability and reusability than other enzyme electrodes reported in the literature.

Figure 6:
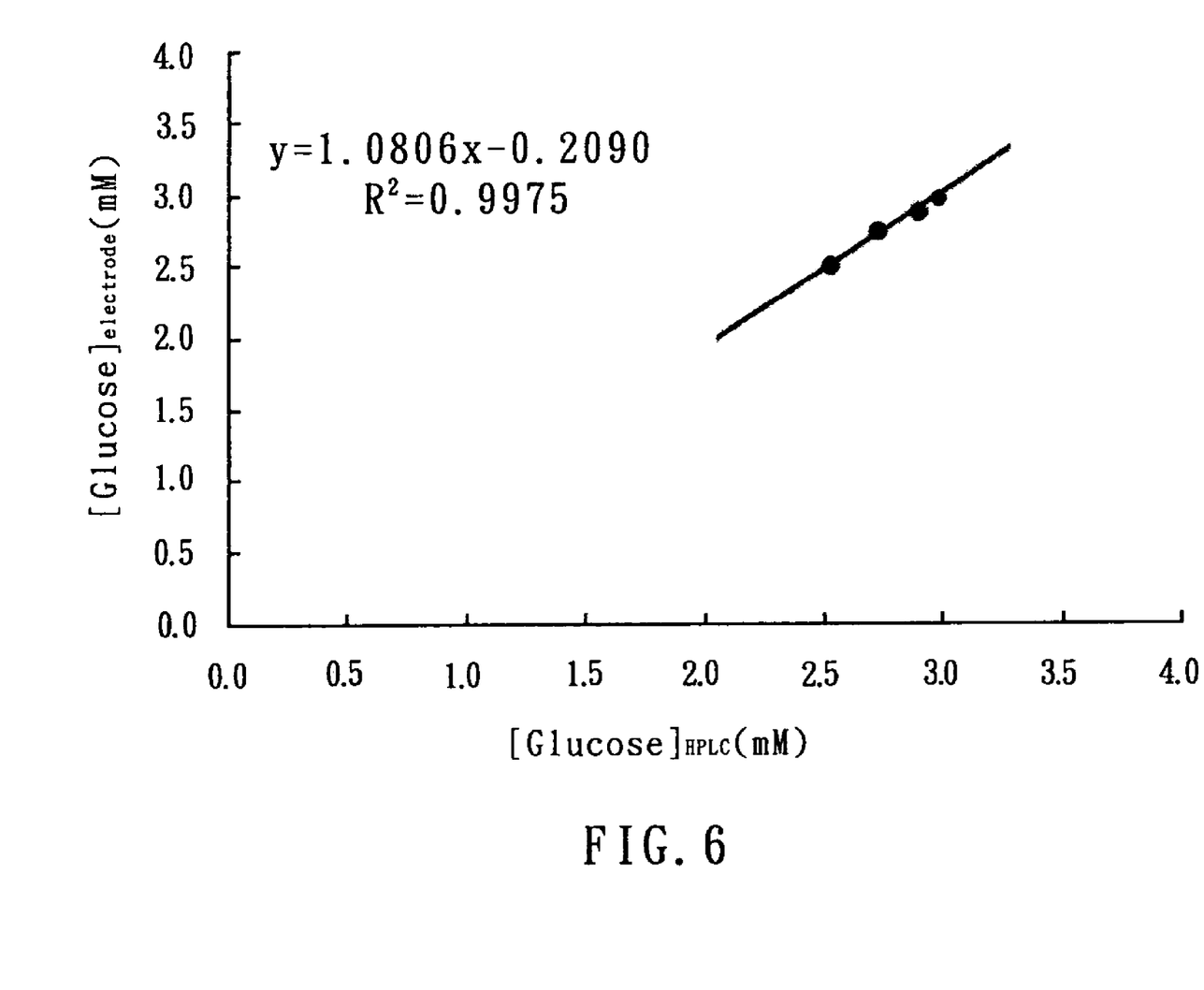
FIG. 6 shows the correlation of the analysis results by the enzyme electrode according to the present invention and by the HPLC.

FIG. 6 shows a correlation of the analysis results by the enzyme electrode according to the present invention and by the HPLC. The linear regression line in FIG. 6 has good linearity ($r^2=0.9975$) and a slope 1.0806 with a 95% confidence interval 0.9920-1.1692 which includes the ideal slope 1.0 of perfect correlated data. Therefore, the analysis results obtained from the two analysis methods are comparable, and no systematic error exists for the enzyme electrode. In addition, calculating the recovery rate of the spiked sample can be used to compare the analysis accuracy of the two methods. The recovery rate of the enzyme electrode method is 98.6% comparable to the recovery rate of the HPLC method of 99.0% meaning equal accuracy of the two methods.

The enzyme electrode produced by the above method may be applied to an electrochemical sensor, which comprises a working electrode and a reference electrode, whereby the enzyme electrode functions as the working electrode. Notice that when functioning as the working electrode, it is possible that only a portion of surface of the enzyme electrode is modified and bounded with glucose oxidase. For example, the whole surface of the enzyme electrode may be deposited with gold, but only a portion such as the end portion or the middle portion of the gold surface may be modified and bounded with the glucose oxidase. In another embodiment of the present invention, the electrochemical sensor may further comprise a counter electrode, and a mediator may be formed on the surface of the working electrode by a coating or screen-printing method. The mediator can be chosen from any publicly known or available products, such as the above-mentioned hydroxymethylferrocene (Fc).

Although specific embodiments have been illustrated and described, it will be appreciated by those skilled in the art that various modifications may be made without departing from the scope of the present invention, which is intended to be limited solely by the appended claims.

What is claimed is:

1. A method for producing an enzyme electrode used to detect glucose, comprising:
    providing a substrate having a carbon surface, wherein the substrate is a pencil lead, and the carbon surface is formed by coating a carbon paste on the surface of the pencil lead;
    forming a gold surface on the carbon surface and thus forming an electrode;
    modifying the gold surface by L-cysteine to bond covalently the gold particles of the gold surface and the sulphydryl group of L-cysteine, thereby forming a first electrode having a first modified surface;
    modifying the first modified surface by N,N'-dicyclohexylcarbodiimide, the L-cysteine of the first modified surface and the N,N'-dicyclohexylcarbodiimide being dehydrated to form covalent bonds, thereby forming a second electrode having a second modified surface; and
    contacting the second modified surface with the glucose oxidase, an amide bond being formed between the L-cysteine group of the second modified surface and the glucose oxidase, thereby forming a third electrode having a third modified surface.

2. The method as recited in claim 1, further comprising a thermal process at about 120° C. for drying the surface of the carbon paste, after the carbon paste is coated on the surface of the pencil lead.

3. The method as recited in claim 1, wherein the gold surface is formed by a deposition, ink-inject, electrodeposition, or screen-printing method.

4. The method as recited in claim 1, wherein the gold surface is formed by electrodeposition in which the gold ions are reduced and deposited on the carbon surface.

5. An enzyme electrode used to detect glucose and produced by the method as follows:
    providing a substrate having a carbon surface, wherein the substrate is a pencil lead, and the carbon surface is formed by coating a carbon paste on the surface of the pencil lead;
    forming a gold surface on the carbon surface and thus forming an electrode;
    modifying the gold surface by L-cysteine to bond covalently the gold particles of the gold surface and the sulphydryl group of L-cysteine, thereby forming a first electrode having a first modified surface;
    modifying the first modified surface by N,N'-dicyclohexylcarbodiimide, the L-cysteine of the first modified surface and the N,N'-dicyclohexylcarbodiimide being dehydrated to form covalent bonds, thereby forming a second electrode having a second modified surface; and
    contacting the second modified surface with the glucose oxidase, an amide bond being formed between the L-cysteine group of the second modified surface and the glucose oxidase, thereby forming the enzyme electrode.

6. The enzyme electrode as recited in claim 5, wherein the enzyme electrode is applied to an electrochemical sensor for the detecting of glucose, the electrochemical sensor comprising a working electrode and a reference electrode, and the enzyme electrode functioning as the working electrode.

7. The enzyme electrode as recited in claim 6, wherein the electrochemical sensor further comprises a counter electrode.

8. The enzyme electrode as recited in claim 6, further comprising a mediator coated on the surface of the working electrode.

9. The enzyme electrode as recited in claim 6, wherein the mediator comprises hydroxylmethylferrocene (Fc).

10. An enzyme electrode used to detect glucose, comprising:
   a substrate structure, said substrate structure comprising a pencil lead, a carbon paste coated on the surface of the pencil lead, and a gold layer covering the carbon paste;
   a modified structure, said modified structure being chemically bound with the gold layer, the modified structure comprising a L-cysteine group and a glucose oxidase group, an Au—S covalent bond being formed between the gold layer and the L-cysteine group, and an amide bond being covalently bound between the L-cysteine group and the glucose oxidase group.

11. The enzyme electrode as recited in claim 10, wherein the enzyme electrode is applied to an electrochemical sensor for the detecting glucose, the electrochemical sensor comprises a working electrode and a reference electrode, and the enzyme electrode functions as the working electrode.

12. The enzyme electrode as recited in claim 11, wherein the electrochemical sensor further comprises a counter electrode.

13. The enzyme electrode as recited in claim 11, further comprising a mediator coated on the surface of the working electrode.

14. The enzyme electrode as recited in claim 11, wherein the mediator comprises hydroxylmethylferrocene (Fc).

* * * * *